United States Patent
Grogan, Jr.

(10) Patent No.: US 10,201,477 B2
(45) Date of Patent: Feb. 12, 2019

(54) DOSE CALCULATING DISPENSER USING A BODY WEIGHT SCALE ON A MEDICINE DROPPER

(71) Applicant: Jack Raymond Grogan, Jr., Iowa City, IA (US)

(72) Inventor: Jack Raymond Grogan, Jr., Iowa City, IA (US)

(73) Assignee: Prophy Research Corporation, Honolulu, HI (US)

( * ) Notice: Subject to any disclaimer, the term of this patent is extended or adjusted under 35 U.S.C. 154(b) by 143 days.

(21) Appl. No.: 15/530,024

(22) Filed: Nov. 21, 2016

(65) Prior Publication Data
US 2018/0140509 A1   May 24, 2018

(51) Int. Cl.
*A61J 7/00* (2006.01)
*A61J 1/00* (2006.01)
*A61M 5/31* (2006.01)

(52) U.S. Cl.
CPC .............. *A61J 7/0046* (2013.01); *A61J 1/00* (2013.01); *A61J 7/0053* (2013.01); *A61M 5/3129* (2013.01); *A61M 2005/3125* (2013.01); *A61M 2205/6063* (2013.01)

(58) Field of Classification Search
CPC ........ A61M 5/3129; A61M 2205/6063; A61M 2005/3125; A61M 2005/3126; A61J 7/0053
See application file for complete search history.

(56) References Cited

U.S. PATENT DOCUMENTS

| | | | | | |
|---|---|---|---|---|---|
| 1,559,978 | A | * | 11/1925 | Page | A61M 5/204 222/390 |
| 2,432,605 | A | * | 12/1947 | Barach | A61M 5/31511 116/227 |
| 6,413,241 | B1 | * | 7/2002 | Slishman | A61J 1/00 604/186 |
| 2002/0088131 | A1 | * | 7/2002 | Baxa | A61M 5/31525 33/494 |
| 2011/0042255 | A1 | * | 2/2011 | Traboulsi | B65D 23/00 206/459.5 |
| 2016/0166776 | A1 | * | 6/2016 | Appelbaum | A61M 5/31525 604/189 |

* cited by examiner

*Primary Examiner* — Susan S Su

(57) ABSTRACT

A dose dispensing device such as a medicine dropper is improved by putting a dosing scale such as a body weight scale directly on the dose dispensing device. This improved device is used to simultaneously calculate and measure an exact dose of liquid medication, based on the body weight of the patient.

4 Claims, 3 Drawing Sheets

DOSE CALCULATING DISPENSER USING A BODY WEIGHT SCALE ON A MEDICINE DROPPER

CROSS-REFERENCES TO RELATED APPLICATION

This application is a continuation-in-part of application Ser. No. 12/456,418, hereby abandoned, which is a continuation-in-part application of application Ser. No. 11/654,808 (abandoned), which is a continuation-in-part application of application Ser. No. 10/453,087 (abandoned), which is a continuation-in-part application of application Ser. No. 09/859,249 (abandoned), which is a continuation-in-part application of application Ser. No. 08/784,284 (abandoned), which is a continuation-in-part application of application Ser. No. 08/501,977 (abandoned), which is a continuation-in-part application of application Ser. No. 08/214,634 (abandoned), which is a continuation-in-part application of application Ser. No. 07/902,358 (abandoned), which is a continuation-in-part application of application Ser. No. 07/716,662 (abandoned), which is a continuation-in-part application of application Ser. No. 07/435,515 (abandoned).

BACKGROUND OF THE INVENTION

1. Field of the Invention

This invention relates to dispensers for liquid medications, and more specifically to medicine droppers.

2. Background—General Art

Until about 100 years ago, doses of most medications were not very exact because the crude drugs were mostly plant extracts of uncertain strength. Doctors gave more to adults and less to children. In about 1870 the science of dosimetry emerged, using the active ingredients of the plant extracts, in exact doses. For the last century medications have been prescribed in an exact form, in an exact dose, and usually based on the body weight of the patient.

Medicine droppers are commonly used to measure and give liquid drugs and nutrients to children. The dropper usually has a scale calibrated in units of volume, usually millimeters (ml), or some fraction of a teaspoon (tsp). Other familiar devices for dispensing liquid medications are oral syringes, cups, measuring cylinders with or without a spoon attached, and measuring spoons.

An early example of using a volume of liquid to measure something other than volume is the mercury thermometer. Galileo Galilei invented the first thermometers (these used density). The first with numerical scales were invented for medical use by Santorio Santorio about 1600. In 1714, Daniel Gabriel Fahrenheit invented the first mercury thermometer. These familiar devices use calibrated marks on the tube to allow the temperature to be read by the volume of the mercury within the tube, which varies according to the temperature.

3. Background—Fluoride Doses for Infants

The current invention came about in the study of one of the most commonly administered liquid medications for children, fluoride in multivitamins. These products were invented independently by at least 3 pediatricians—Peebles, Margolis, and Hamberg. Brands such as Poly-Vi-Flor® became exceedingly popular starting in about 1962, and probably about a fourth of children born since then have had them. (About the only kids who did not were those who lived with fluoridated water, which is about half the country, and those who did not go to a pediatrician for some reason.)

Fluoride prevents dental caries, which is also called tooth decay or cavities. The published clinical trials of the fluoride-vitamin products showed excellent results. Cavities were reduced by at least half, and in some trials up to 80%. Many kids reached adulthood completely cavity-free.

However, there was a slight problem that came along with the marvelous cavity prevention: white spots on teeth. Most trace nutrients are at least fairly dose sensitive (iron and copper are well known examples). Fluoride is very dose sensitive.

Too little fluoride causes tooth enamel to be poorly formed. The poor enamel can be seen at most levels of magnification, and many people can recognize the difference with the naked eye. The biggest and most easily seen effect of fluoride deficiency is pits and fissures in the enamel of the molar teeth. The most well known effect of fluoride deficiency is tooth decay, which is predisposed by the poor enamel.

Just right fluoride causes gorgeous enamel that has a fine white color and a luster that looks like the inside of a sea shell. If a set of teeth has the right amount of fluoride for the entire time it is forming (from early pregnancy until the teen years), every part of every tooth will look good and never have tooth decay.

Too much fluoride causes visible changes in the enamel. Large overdoses (about 8 to 16 times the ideal amount) cause very serious brown staining and pitting of the enamel. Smaller overdoses (about 2 to 4 times the ideal amount) cause teeth to have a chalky white appearance. At still smaller overdoses, teeth are a little whiter than normal, or lose a little of their translucency, but only a professional would recognize the condition as very mild fluorosis.

There are two factors that complicate fluoride dosing of infants. The first is the teeth that are growing at that time. Some are particularly sensitive to too little fluoride, and others are particularly sensitive to too much fluoride. The two areas where we would like to prevent cavities are the first permanent molars (very important teeth that help keep the rest of the teeth straight, and that are very cavity-prone without fluoride) and the front baby teeth. The front baby teeth, up near the gum line, are sometimes attacked by "bottle rot" (which requires an expensive and risky repair). The growing teeth that we would like to protect from too much fluoride are the permanent front teeth. The part of these teeth that is forming is the leading edge, and this is the part of a smile that shows the most. It is the last place you would want to have a cosmetic defect like a white spot.

The second complicating dosage factor is the rapid growth of a newborn. At birth most infants weigh between 6 and 9 pounds. This weight is usually doubled by age 6 months, and by age 2 years most weigh between 20 and 35 pounds. So there is a body weight that is changing about 6 fold, and a dosage sensitivity of about two fold.

(A minor third complication is the time it takes to see the results.

When a doctor prescribes fluoride at birth, the teeth that are affected will not be fully visible until about age 10 years. This makes it very difficult to develop a "feel" for these doses.)

Fluoride is usually prescribed for a long period of time, since the child will need it every day during childhood. Historically fluoride has been prescribed by age even though it is well known that the optimum would be to prescribe it by weight. For example, children born during the 1960's and 70's were prescribed 0.5 mg/day from birth to age 3 years, then 1 mg/day. This dosage schedule caused a very common and very recognizable pattern of cavities and white spotting:
1. Cavities: almost none. Half the kids have only 4 cavities (fillings now) in a very specific place. The 6th tooth back from the front, one in each corner of the mouth. And only on the chewing surface of those teeth. (These are the first permanent molars. The chewing surfaces form in pregnancy just before the fluoride started at birth, so got cavities. The rest of these molars, and the rest of the permanent teeth, formed after birth, so got fluoride and no decay.)
2. White spots: lots. More than half the kids had white spots on the leading edge of their permanent front teeth, the precise part of the tooth that formed at birth when the doses were the highest relative to the small body size. By the time the rest of the tooth formed, the children had grown into their doses and the enamel looks great just above the white spots.
(Further reading: Aasenden R, Peebles T C. Effects of fluoride supplementation from birth on human deciduous and permanent teeth. *Arch Oral Biol* 1974; 19:321 and 1978; 23:111.)

So far the general response to the challenge of how to get the right dose of fluoride has been to revise the dosage table. It has been considered impractical to give each child a dose exactly by body weight, every day of childhood.

Children born today (2016, and since May 1995) in the USA are generally not given any fluoride for the first 6 months of infancy. Then at age 6 months they start on a slightly lower schedule than in the recent past. If clinical trials and common sense are any indication, by the time these kids are about 5 years old it will be obvious that these kids will see an increase in tooth decay over the course of their childhood. They should have more cavities than their parents who were born in the 60's, 70's, and 80's with relatively high fluoride. However, the new kids will still have far less cavities than their grandparents born in the days before fluoride became popular. By the time the new kids are about 10 years old it will probably be seen that the fluorosis is almost as prevalent as before. However, it should be a little different. It should be milder (doses being lower). And it should have shifted up on their front teeth about ⅛' of an inch since the sudden increase in fluoride will have happened at age 6 months rather than at birth like before.

Prophy Research Corporation will keep a web site that will give you the latest opinions on the best way to have your kids' teeth look great and have no cavities. The title is "Infant fluoride and the OptiDose® dropper—by Ray Grogan". Lately search engines like Yahoo!® and Google™ make it the number one site if you just search for "infant fluoride optidose" (without quotation marks). Here are a few methods that work fine without getting involved with the current invention. (There are even more methods on the web site.)

A method that could do the same thing without a dose by weight dropper is to just eyeball the doses on a regular dropper. If you look at a dose by weight dropper, you'll see a full dropper (1 ml) is 16 pounds, and a half full dropper is 8 pounds. From that you can construct fairly simple directions to go with a plain 1 ml dropper. The simplest would be to start at birth with a half full dropper and by age 6 months be up to a full dropper.

One team has devised another way that has worked very, very well. The Drs. Glenn of Miami have experimented with providing fluoride in pregnancy, which is when tooth development begins (most of the baby teeth are formed in pregnancy). Their several thousand patients have had excellent dental health (about 95% completely cavity-free, beautiful teeth) regardless of what followed pregnancy. While most have had some combination of fluoridated water, plain fluoride, and/or fluoride in vitamins, the fluoride in pregnancy seems to be a very important beginning. (In December 2000 the Glenns published a useful and amusing book, *How to have children with perfect teeth*.)

Having a relatively high amount of fluoride in pregnancy, followed by a relatively low amount during infancy, is probably fairly close to the "natural" model. (Primitive diets for adults and older children were relatively high in fluoride from lots of rough plant materials, animal foods such as bone marrow, and seafoods. During infancy breast milk was the sole food, and that is relatively low in fluoride. Primitive people had almost perfect teeth. There was enough dietary fluoride to cause fluorosis occasionally.)

Another method just for infancy involves a special water and powdered formula. This one would work especially well following prenatal fluoride, as the fluoride from pregnancy seems to extend well into infancy via fluoride reserves stored in the teeth, bones, and other infant tissues (similar to iron reserves). This should suffice during the period of breast feeding (usually less than 6 months nowadays). Once a child is switched to formula the new method can begin. To get the fluoride intake perfect when using powdered formula, use a commercial baby water. (Examples: Beech-Nut® Spring Water with Fluoride, Nursery® Water by DS Services, and various private label brands from large supermarkets and pharmacies.) All of these have about 0.5-0.7 mg F, which is about half the strength of fluoridated water. Overall this is one of the easiest and best methods of getting perfect fluoride. Since feeding automatically parallels growth, the dosage will take care of itself. By starting in pregnancy, and by getting through infancy with a very gentle dosing, the remainder of childhood can be dosed according to the regular pediatric dosage schedule. Please ask your pediatrician for help with dosing anything for your children.

Now please give me one minute to express the biggest problem in creating big healthy smiles. I do NOT have a solution. To be brief I am going to be blunt. Our system generally pays our doctors and dentists only if patients have trouble, which is fine for most medicine, but horrible for fluoride and other nutrients that work best at preventing things like cavities, and maybe giving a child straighter teeth. Some of these effects are not seen for 10 to 20 years after the action (or lack thereof), starting before pregnancy. Designing a new and better reward system should be possible, but it is not at all clear to me how to even begin. Good luck and thank you to future inventors.

4. Background—Specific Art (Dispensing Devices)

The most well-known prior art is ordinary medicine droppers. Existing medicine droppers have volume scales, which are usually labeled with ml, cc, tsp, OZ, and the like, These can be used to dose by body weight, IF you have a dosage table, or have the dosage (usually in mg/kg) and concentration (usually mg/ml) necessary to do your own calculations. However, mistakes are made. For example, in the Dec. 4, 2002 *Wall Street Journal*, the page D3 headline is "Drug dosing is major cause of hospital errors". Here is a quote: "For children, the problem often stems from a miscalculation when converting weight from pounds to kilograms, leading to improper dosing." (Patent citations: Munch, U.S. Pat. No. 1,533,753 shows a metal casing that slips over a medicine dropper to add a volume scale, "whereby the plain glass element may be used to measure various quantities of liquid". George U.S. Pat. No. 4,693,709 for syringes and Swartwout U.S. Pat. No. 4,416,381 for cups.)

There are two candidates for the closest prior art. Physically it is probably the dispenser introduced with Zimecterin in 1984. This dispenser uses an oral syringe with a body weight scale on it, with the scale going from full to empty as the syringe is filled. In other words, when the syringe holds the least the scale reads at its maximum. This is because this dispenser comes fully loaded, and the scale is used as the medication is used up. It could not be used to be filled to the body weight of a patient on the scale. For example, if one of these prior art scales went from zero to 100 pounds, and it were filled to the 10-pound mark, it would actually be filled to 90% of its volume, or to a 90-pound dose. However, it works absolutely fine as designed. If it were completely filled (which is how it comes), and the plunger is pushed down to the 10-pound mark, the syringe would dispense 10% of its volume, the correct 10-pound dose. (Sold by Farnam Companies, Inc/ 301 West Osborn/POB 34820/Phoenix, Ariz. 85067-4820. Advertised in Tack 'n Togs, November 1984. This type of dispenser is now almost universal in similar animal medications. The roots may go back to Page (U.S. Pat. No. 1,559,978, 1926).) Functionally the closest prior art is a medicine cup with child and adult doses.

This cup is shown (incidentally) in UK 364,528 (Wadsworth, 1931, FIG. 9), or in a contemporary commercial product, COMTREX® Bristol-Myers© 1987 (until labeling for children was stopped in about 1992). This child-adult cup is filled with a dose that is roughly the size of the patient. It is easy to use and only requires one piece. It does not use a numerical scale, and it is not accurate. It does not, for example, distinguish between a 25-pound child and a 100-pound child.

The Janssen device described next does not meet any of the criteria of 35 U.S.C. 102 (a) or (b) and is therefore not considered prior art.

In Europe Janssen has pioneered a new type of dosing device that has the potential to solve many dosing problems. (First commercial use in Prepulsid® (cisapride) in Switzerland, 1989; later used with Hismanal® (astemizole) in Panama, 1990, now used in about 20 products around the world.) These elegant devices, which use a body weight scale on an oral syringe, allow precise dosing of each child. This is substantially the same as FIG. 4 of the current invention. In private Janssen had working models well before the current invention. Janssen did not sell or publish their invention before the date of the current invention.

Another non-prior art reference: A contemporary physician, Dr. Sam Slishman, also invented dispensers to dose by body weight while working on ways to get quick doses in medical emergencies (U.S. Pat. No. 6,413,241, 2002). The coolest thing that Dr. Slishman did with his invention was to come up with a way he could let people use it. This way fits what people have come to expect—google, download, print and use for free. http://www.slishman.com/pediatric-dosing-syringes (or google Slishman dosing).

Another non-prior art reference: A contemporary pharmaceutical executive, Michael A. Creaturo, also invented dispensers to dose by body weight, while working on dosage safety with injection syringes (U.S. Pat. No. 9,192,723, 2015 and U.S. Pat. No. 9,302,050, 2016). His oral syringes can be seen at http://www.asepsismedical.com/dose-2-weight-syringe/ (or google dose-2-weight).

There is prior art that is purely about using well-placed indicia to save a calculating step. Miller invented a measuring cup for bakers who want to make some fractional part of a full recipe (for example, making one loaf of bread from a recipe that normally makes three loaves). His cup looks just like a regular measuring cup, only it is shrunk to one-third the size, and has a label saying "⅓ recipe". (The Court of Customs and Patent Appeals threw out a "printed matter" objection and said that it was new and unobvious.) (217 USPQ 401 and 164 USPQ 46.)

There have been other attempts to dose according to body size. Both Dr. Darbon (French patent #70.09318, 1971) and Dr. Broselow (U.S. Pat. No. 5,010,656, 1991) have each proposed devices that calculate an accurate dose of medication, based on body size, as some other task is being performed (mixing the drug in Darbon's case and measuring the patient in Broselow's). These devices are very accurate, but both require two pieces and two steps to use. Dr. Broselow's system is based on a length measuring tape with coded zones and dispensers coded to the tape. It is inexpensive, easy to use, and would work better than the status quo for fluoride and many other pediatric medications.

Another well known way to express body size is body surface area, or BSA, which is calculated from height and weight.

An interesting use of scales on insulin syringes is a box to surround the syringe, with 4 scales, each scale showing volume units in a different concentration. (Barach U.S. Pat. No. 2,432,605, 1947.)

A slide calculator has been used in determining dosages, with body weight, height, and age scales on it (Ausman U.S. Pat. No. 4,308,450, 1981). His scales are quite similar to my weight, height, and age scales. And the purpose is similar, to calculate a weight-based dose. However, Ausman just calculates the dose. He does not have any kind of dosage dispenser included.

The final citation shows that a volume scale on a container can be used to calculate some other related number (a bucket to calculate amount of cattle feed based on amount of milk given). (Naatz, U.S. Pat. No. 1,865,034, 1932.)

SUMMARY OF THE INVENTION

Dose calculating dispensers are used with liquid medications and come in several forms. A dose by weight medicine dropper is made by marking a simple body weight scale directly on a medicine dropper. To get an exact dose, all a parent has to do is fill the dropper up to the body weight of his or her child on the numerical scale. The scale works by converting volume into a more usable measurement of dose per body weight. The dropper becomes, in essence, a combined medicine dropper and dosage calculator. Similar dose calculating dispensers can be made with oral syringes and medicine cups, and with other scales based on body length, body surface area, and age.

Figure 1:
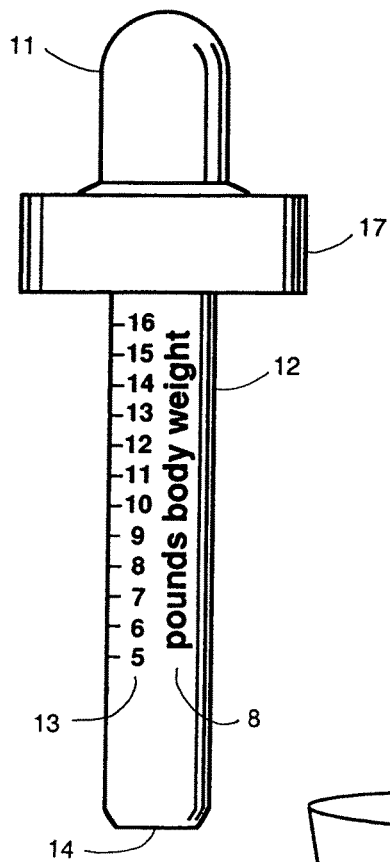
FIG. 1 is a side perspective view of a medicine dropper graduated with a body weight scale, in accordance with this invention.

| REFERENCE NUMERALS USED ON DRAWINGS | | |
| --- | --- | --- |
| Reference numeral | FIG. | What is shown |
| 8 | 1 | identifying label |
| 10 | 1, 2, 6 | medicine dropper |
| 11 | 1 | flexible bulb |
| 12 | 1 | tube |
| 13 | 1, 3, 4 | body weight scale |
| 14 | 1, 4 | opening |
| 15 | 2 | body length scale |
| 16 | 3 | medicine cup |
| 17 | 1 | bottle cap |
| 18 | 3 | age scale |
| 20 | 4 | oral syringe |
| 22 | 5 | prescription label |
| 24 | 5 | patient's current age |
| 26 | 5 | patient's current weight |
| 28 | 4 | tube-like reservoir |
| 30 | 4 | plunger |
| 32 | 3 | cylinder-like reservoir |
| 34 | 6 | body surface area scale |

DESCRIPTION OF THE PREFERRED EMBODIMENT

FIG. 1 shows a dose by weight medicine dropper. A conventional medicine dropper 10 is made from a tube 12 with an opening 14, flexible bulb 11, and usually a bottle cap 17. The unique feature of this invention is marking tube 12 with a body weight scale 13. An identifying label 8 may be added for extra clarity.

Other than having body weight scale 13 and identifying label 8 marked on it, a dose by weight medicine dropper is not different from familiar medicine droppers. Body weight scale 13 has the function of converting a volume of medication into a useful dosage in pounds body weight.

Medicine dropper 10 is graduated with body weight scale 13 such that body weight indicators on the scale indicate doses that are desired for those body weights. For example, if 0.7 ml is the dose desired for an 11 pound infant, an 11 pound mark is placed where the dropper holds 0.7 ml.

Body weight scale 13 contains at least two discrete numerical points in a series, such that a change in volume corresponds to a change in pounds body weight. Body weight scale 13 is self-contained in the sense that in it is all the dosage information needed, presuming the user already knows the weight of the patient. The user does not require dosage tables or other information sources. Body weight scale 13 does not refer to codes or other information that is not understandable in and of itself. Body weight scale 13 is on medicine dropper 10 so that the scale 13 is used to calculate a dose when the tube 12 is filled to the body weight of the patient, in one easy step and with one simple tool. When the dose is calculated by the scale 13, there is no need for a separate traditional method of calculating body weight doses, such as dosage tables, manual or electronic calculations, etc. The numerical points on scale 13 directly represent numeric body characteristic dimensions such as weight in this case.

Body weight scale 13 may be labeled with identifying label 8 "pounds body weight" to prevent confusion with ordinary volume scales which are usually labeled with ml, cc, tsp, oz, and the like. Body weight scale 13 uses only conventional measuring units that are already used to measure body weight, such as pounds or kilograms.

The basic and novel feature of the body weight scale 13 (and the others on length, age, and BSA) is the easy dose calculating. A product that uses these scales would usually include other things common to pharmaceutical products— starting with a bottle of medication and its box. In some cases it would include a (prior art, of course) volume scale such as shown on medicine cup 16. There are also things that are excluded. The "reverse" scales of Zimecterin and Page are excluded, as are all of the design elements that go with them, as all of these distract from the easy dose calculating.

| | Zimecterin (horse dewormer) | The claimed invention |
| --- | --- | --- |
| Scale direction | Ascending | Descending |
| Container | Self-contained (the syringe comes pre-filled) | Bottle (and usually a bottle cap with hole for syringe or dropper to slide thru) |
| Viscosity | Paste | Liquid |
| Syringe end cap | Yes | No |
| Syringe end opening | Relatively large (like 8 mm) | Relatively small (like 2 mm for Janssen) |
| Lock and notches (threads) | Yes | No |
| Instructions for second dosing | Yes | No |

Body length scale 15 is labeled with identifying label "inches body length" to prevent confusion with ordinary volume scales or Dr. Broselow's length codes. (This label may be similar words or units, and may be located anywhere on dropper, in dosing instructions, etc. as long as the scale is identified.) A dropper designer may want to label the scale in a variety of ways (e.g., body length, inches body length, heel-to-crown, inches, centimeters, etc.). The scale could also be identified in the package insert, dosing instructions, etc. A dropper coded as below in dosing table 1 has a body length scale because the "code" is not really a code, it is the body length:

| Dosing table 1 Dosing instructions: find body length in the table below and fill dropper to the code. | |
| --- | --- |
| Body length (in.) | Code |
| 28 | 28 |
| 27 | 27 |
| 26 | 26 |
| . . . | . . . |

Droppers coded as below in dosing tables 2 and 3 do NOT have a body length scale:

Dosing table 2
Dosing instructions: find body length in the
table below and fill dropper to the code.

| Body length (in.) | Code |
|---|---|
| 28 | Red |
| 27 | Blue |
| 26 | Yellow |
| ... | ... |

Dosing table 3
Dosing instructions: find body length in the
table below and fill dropper to the code.

| Body length (in.) | Code |
|---|---|
| 28 | 10 |
| 27 | 9 |
| 26 | 8 |
| ... | ... |

Figure 3:
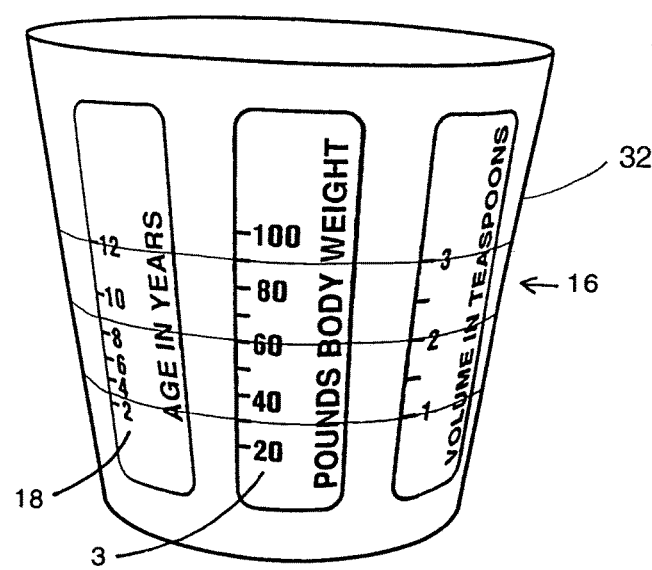
FIG. 3 is a side perspective view of a cup graduated with a body weight scale and an age scale, in accordance with this invention.

An age scale 18 on medicine cup FIG. 3 is labeled with identifying label "age in years" and is unlikely to be confused with Wadsworth's child-adult doses. Other designs could be a little closer. Cups with indicia as below in table 4 do NOT have an age scale because they do not meet requirements such as "numerical" (A) or "discrete" (B).

TABLE 4

| A<br>Descriptive | B<br>Age (years) in ranges |
|---|---|
| Great big child | 10-12 |
| Medium child | 8-10 |
| Wee baby | 6-8 |
| ... | ... |

Figure 2:
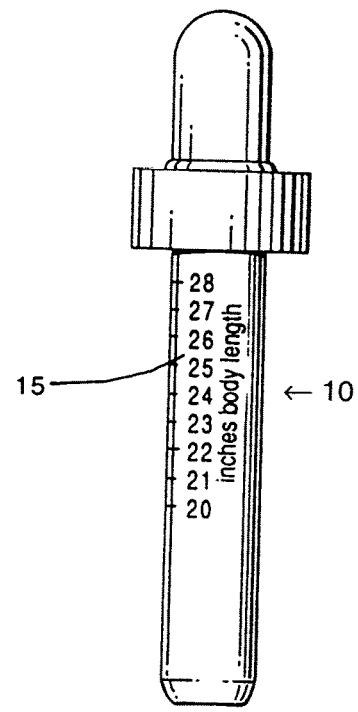
FIG. 2 is a side perspective view of a medicine dropper graduated with a body length scale, in accordance with this invention.
Figures 4, 5:
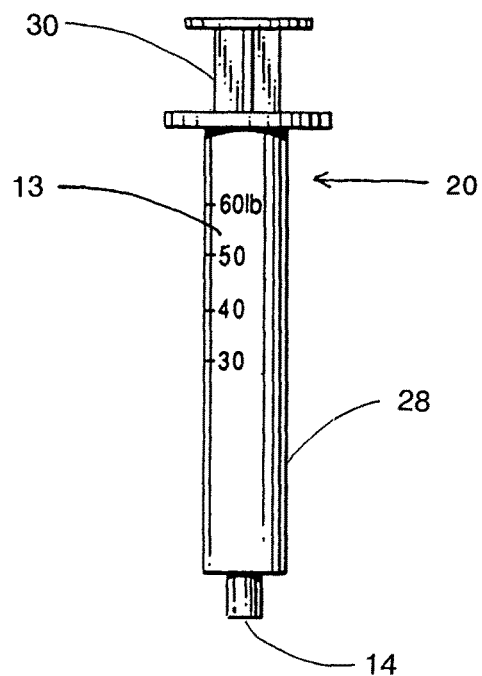
FIG. 4 is a side perspective view of an oral syringe with a body weight scale on it, in accordance with this invention.
FIG. 5 is a front view of a prescription label with a patient's current body weight and age.
Figure 6:
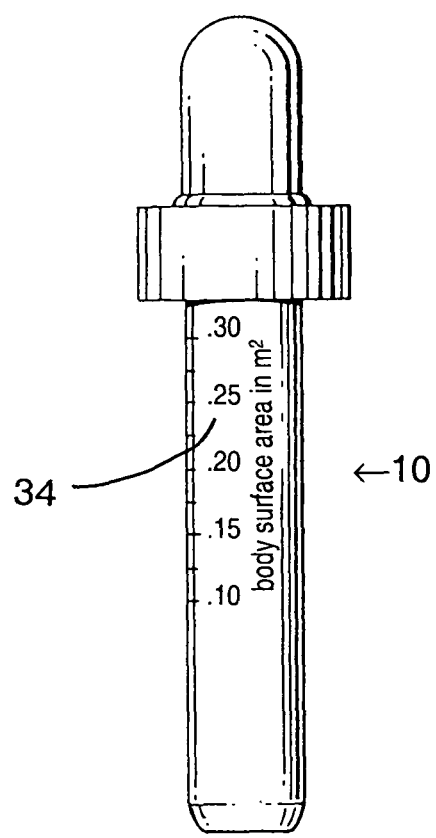
FIG. 6 is a side perspective view of a medicine dropper graduated with a body surface area scale, in accordance with this invention.

Additional embodiments for dose calculating dispensers are shown in FIGS. 2, 3, 4, and 6. Scales may be made for children and adults of various sizes. FIG. 2 shows an embodiment similar to FIG. 1, except based on a body length scale 15 visible upon medicine dropper 10. Body length scale 15 also uses only conventional measuring units that are already used to measure body length, such as inches or centimeters. FIG. 3 shows a medicine cup 16 with 1 to 4 scales visible upon the dispenser, in this case a body weight scale 13 and an age scale 18 marked on the cylinder-like reservoir 32 with a closed bottom and an open top. Age scale 18 also uses only conventional measuring units that are already used to measure age, such as months or years. (FIG. 3 incidentally shows an ordinary volume scale, this one calibrated in teaspoons (tsp). This scale is prior art and not one of my improvements.) FIG. 4 shows an oral syringe 20 with body weight scale 13 visible upon the tube-like reservoir 28. A plunger 30 slides within the tube-like reservoir 28 at the top end. There is an opening 14 at the bottom end of the tube-like reservoir 28. As the plunger 30 is pulled up, away from the opening 14, the volume in the reservoir increases and the value indicated on body weight scale 13 increases. The body weight scale 13 is directionally proportional to the volume in the reservoir 28. FIG. 5 shows a prescription label 22 with a patient's age 24 and weight 26, which may be used for extra clarity. FIG. 6 shows an embodiment similar to FIG. 1, except based on a body surface area scale 34 on medicine dropper 10. Body surface area scale 34 also uses only conventional measuring units that are already used to measure body surface area, such as square feet or square meters.

The term "body characteristic . . . used to measure body size" is used to encompass all of the listed ways doctors and parents use to say how big a patient is, namely weight, length, surface area, and age. It does not include body characteristics that are not primarily about body size, even if they are used for dosing, such as degree of insulin resistance, number of gene repeats (as in Huntington's disease), muscle-to-fat ratios, etc.

As in a thermometer, the position of the numbers and scales is critical to function. In all scales (13, 15, 18, and 34), the scale is positioned such that as the dispenser is filled to a specific number (for example 5 pounds) the dispenser calculates and contains the dose for a patient of that body size (in this example, the dose for a 5 pound child).

Another phrase that describes this invention is an apparatus for selection of drug dosages for therapeutic treatment of a patient consisting of a directionally proportional body weight scale marked on a dispensing means.

Other phrases that describe this invention are "a weight of patient indicator for a medicine dropper" and "patient weight indicia on medicine dropper". (This is paraphrasing a contemporary invention by Chanoch, 1997, U.S. Pat. No. 5,645,534. He put a time scale on an insulin injector so that the patient could set it as a reminder of the time of the last injection.) The medicine dropper would consist of a tube, a flexible bulb attached to one end of the tube, an opening at the other end of the tube, and a plurality of indicia on the tube representing a range body weights for a targeted group of patients (such as infants), said indicia including and displaying a weight mark to be chosen for a specific weight of a patient (such as 7 pounds, 8 pounds, 9 pounds, etc.), that weight mark corresponding to a volume of a desired dose to be dispensed when the medicine dropper is filled to that weight mark.

In operation a dose by weight medicine dropper is filled with medication up to the weight of a patient on body weight scale 13. and then the medication is given in the usual fashion.

PRIOR UNITED STATES APPLICATIONS

| Application Number | Filing Date | Status - patented, pending, abandoned |
|---|---|---|
| 07/435,515 | Aug. 4, 1989 | abandoned |
| 07/716,662 | Jun. 13, 1991 | abandoned |
| 07/902,358 | Jun. 23, 1992 | abandoned |
| 08/214,634 | Mar. 18, 1994 | abandoned |
| 08/501,977 | Jul. 3, 1995 | abandoned |
| 08/784,284 | Jan. 15, 1997 | abandoned |
| 09/859,249 | May 17, 2001 | abandoned |
| 10/453,087 | May 31, 2003 | abandoned |
| 11/654,808 | Jan. 18, 2007 | abandoned |
| 12/456,418 | Jun. 11, 2009 | abandoned |

The invention claimed is:

1. A dispenser for measuring and dispensing liquid medication, the dispenser consisting essentially of:
   a medicine dropper, an oral syringe, or cup; and
   a single scale visible on said dispenser,
   wherein the single scale has a series of discrete numerical points,
   wherein the single scale corresponds to a measuring unit, the measuring unit being conventionally used in measuring a body size characteristic, said body size characteristic being selected from one of body weight, body length, body surface area, and age, the dispenser configured such that when a user fills the dispenser to the one of said discrete numerical points on the single scale according to a patient's body size characteristic, the dispenser measures a dose of liquid medication that is suitable for said patient.

2. The invention claimed is:

a dispenser for measuring and dispensing liquid medication, the dispenser consisting essentially of:

a medicine dropper, an oral syringe, or cup; and two to four separate scales visible on said dispenser, wherein each of the two to four scales has a series of discrete numerical points, wherein a first of the two to four scales may correspond to a volumetric first measuring unit, wherein each of the second to fourth scales corresponds to second to fourth measuring units, respectively, each of the second to fourth measuring units being conventionally used in measuring a unique body size characteristic, said body size characteristic being selected from one of body weight, body length, body surface area, and age, the dispenser being configured such that when a user fills the dispenser to one of said unique discrete numerical points on one of the second to fourth scales according to one body size characteristic of a patient, the dispenser measures a dose of liquid medication that is suitable for said patient.

3. The invention claimed is:

a dispenser for measuring and dispensing liquid medication, the dispenser consisting essentially of:

a medicine dropper, an oral syringe, or cup; and a single scale visible on said dispenser, wherein the single scale has a series of graduated lines corresponding to a series of discrete numerical points, wherein the single scale corresponds to a measuring unit, the measuring unit being conventionally used in measuring a body size characteristic, said body size characteristic being selected from one of body weight, body length, body surface area, and age, the dispenser configured such that when a user fills the dispenser to the one of said discrete numerical points on the single scale according to a patient's body size characteristic, the dispenser measures a volumetric dose of liquid medication that is suitable for said patient.

4. The invention claimed is:

a dispenser for measuring and dispensing liquid medication, the dispenser consisting essentially of:

a medicine dropper, an oral syringe, or cup; and two to four separate scales visible side-by-side on said dispenser, wherein each of the two to four scales has a series of graduated lines corresponding to a unique series of discrete numerical points, wherein a first of the two to four scales corresponds to a volumetric first measuring unit, wherein each of the second to fourth scales corresponds to second to fourth measuring units, respectively, each of the second to fourth measuring units being conventionally used in measuring a unique body size characteristic, said body size characteristic being selected from one of body weight, body length, body surface area, and age, the dispenser being configured such that when a user fills the dispenser to one of said unique discrete numerical points on one of the second to fourth scales according to one body size characteristic of a patient, the dispenser measures a dose of liquid medication that is suitable for said patient and allows the user to see a volumetric measurement of said dose of liquid medication in said volumetric first measuring unit on said first scale.

* * * * *